United States Patent
Günther et al.

(10) Patent No.: US 9,511,181 B2
(45) Date of Patent: Dec. 6, 2016

(54) DEVICE AND METHOD FOR BLOOD TREATMENT WITH SINGLE NEEDLE OPERATION

(75) Inventors: Goetz Günther, Oberursel (DE); Andrea Günther, legal representative, Oberursel (DE); Richard Robert Bernd Günther, legal representative, Stuttgart (DE); Gesa Dagmar Günther, legal representative, Stuttgart (DE); Michael Herrenbauer, Neu-Anspach (DE); Martin Lauer, St. Wendel (DE); Ralf Müller, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1790 days.

(21) Appl. No.: 12/602,906

(22) PCT Filed: May 31, 2008

(86) PCT No.: PCT/EP2008/004353
§ 371 (c)(1),
(2), (4) Date: Mar. 15, 2012

(87) PCT Pub. No.: WO2008/148505
PCT Pub. Date: Dec. 11, 2008

(65) Prior Publication Data
US 2012/0251998 A1    Oct. 4, 2012

(30) Foreign Application Priority Data
Jun. 4, 2007  (DE) .................. 10 2007 026 009

(51) Int. Cl.
*A61M 37/00*  (2006.01)
*A61M 1/30*  (2006.01)

(52) U.S. Cl.
CPC .............. *A61M 1/30* (2013.01); *A61M 1/306* (2014.02); *A61M 2205/07* (2013.01)

(58) Field of Classification Search
CPC ........ A61M 1/14; A61M 37/00; A61M 1/00; A61M 1/30; A61M 1/306
USPC ....... 435/2; 422/44; 604/4.01–6.16; 210/645
See application file for complete search history.

(56) References Cited

U.S. PATENT DOCUMENTS

| 4,655,742 A | 4/1987 | Vantard |
| 5,141,490 A * | 8/1992 | Fujii ................ A61M 1/30 210/195.2 |

FOREIGN PATENT DOCUMENTS

| CA | 1 034 206 | 7/1978 |
| DE | 2 441 210 | 3/1975 |

(Continued)

OTHER PUBLICATIONS

PCT International Search Report and Written Opinion for PCT/EP08/004353, mailed on Apr. 6, 2009.

*Primary Examiner* — Philip R Wiest
(74) *Attorney, Agent, or Firm* — Kilyk & Bowersox, P.L.L.C.

(57) ABSTRACT

The present invention relates to a device and a method for blood treatment in a single-needle operating mode. The blood treatment device has an extracorporeal blood circuit comprising a blood supply line leading to the inlet of a blood treatment unit and a blood return line leading away from the outlet of the blood treatment unit. Blood collecting means, for example a blood collecting container, is provided in the blood return line, said means being connected to means for storing gas, for example an air reservoir, by a flow line. The flow connection comprises two line branches, one branch being used to transfer gas from the air reservoir into the blood collecting container and the other branch being used to transfer gas from the blood collecting container into the air reservoir. The connection branch for transferring gas from the air store into the blood collecting container contains means for compressing air, for example a compressor. The device according to the present invention may be operated in such a way that the filling level of the means for collecting blood can be determined as precisely as possible.

16 Claims, 3 Drawing Sheets

(56) References Cited

FOREIGN PATENT DOCUMENTS

| DE | 10 2005001779 | 9/2006 |
| EP | 0 405 094 | 1/1991 |
| EP | 0 472 480 | 2/1992 |

* cited by examiner

DEVICE AND METHOD FOR BLOOD TREATMENT WITH SINGLE NEEDLE OPERATION

FIELD OF THE INVENTION

The present invention relates to a device for blood treatment for single-needle operation, which comprises an extracorporeal blood circuit which has a blood supply line leading to the inlet of a blood treatment unit and a blood return line departing from the outlet of the blood treatment unit, whereby the blood supply line and blood return line lead to a common needle (cannula) and, respectively, lead away from a common needle. Furthermore, the present invention relates to a method for blood treatment in the single-needle operation.

BACKGROUND

Blood treatment apparatuses with a blood treatment unit through which a patient's blood flows are generally known. These include, for example, the known hemodialysis, hemofiltration or hemodiafiltration apparatuses. The known blood treatment apparatuses can be operated in the single-needle or double-needle operation.

With the double-needle technique, the blood is drawn off from the patient's blood vessel via a first needle, conveyed into the blood treatment unit of the blood treatment apparatus and returned into the patient's blood vessel via a second needle. For the removal and return of the blood, use is made of exchangeable hose systems with a blood supply line and blood return line, to which the two needles are connected. The hose systems, which are to be thrown away, are also referred to as disposables.

With the single-needle technique, the removal and return of the blood takes place via a single needle. The blood removed from the patient is stored in a reservoir during an arterial phase, in order then to be returned in a venous phase from the storage unit into the patient's blood system through the same needle.

A blood treatment apparatus for the single-needle operation is known from EP-A-0 472 480 B1. In an embodiment of the known blood treatment apparatus, two blood expansion chambers are provided for temporary storage of blood, which are disposed upstream and downstream of the blood treatment unit. The blood treatment apparatus has a control device, which keeps the pressure in the expansion chambers essentially constant. Level sensors are provided in order to detect the level of the liquid in the expansion chambers.

DE 10 2005 001 779 A1 describes a set for a disposable for the operation of a blood treatment apparatus in the single-needle or double-needle operation. Apart from the blood supply line and blood return line for the connection to the blood treatment unit, the disposable comprises an expansion unit which can be coupled to the air separation unit in order to increase the volume for the single-needle operation. During the single-needle operation, blood is conveyed through the blood supply line into the blood treatment unit and out of the blood treatment unit into the air separation and expansion unit in the arterial phase, the blood supply to the patient being interrupted. A predetermined pressure is built up in the air separation and expansion unit, which is monitored by means of a pressure measuring unit. By means of a compressed air unit, a predetermined pressure can be established in the expansion and air separation unit by actuating an air pump which is incorporated between a tank and the expansion unit. Moreover, it is proposed to calculate the blood volume in the expansion and air separation unit with the aid of the measured values from three pressure sensors and the known system volumes. Furthermore, it is proposed to use the air pump to regulate the pressure in the venous phase, so that the delivery rate of the blood can be adapted in the optimum fashion.

An object of the present invention is to provide a device for blood treatment for the single-needle operation, wherein the blood volume in the blood reservoir can be ascertained without level sensors and the behavior in the case of malfunction can be improved. Moreover, it is an object of the present invention to provide a blood treatment method in the single-needle operation, wherein the blood volume in the blood reservoir can be ascertained without level sensors and the behavior in the case of malfunction can be improved.

SUMMARY

The device for blood treatment according to an example embodiment of the present invention comprises an extracorporeal blood circuit, which has a blood supply line leading to the inlet of a blood treatment unit and a blood return line departing from the outlet of the blood treatment unit. This extracorporeal blood circuit with the blood treatment unit does not have to be part of the blood treatment device, but may be a disposable intended for single use, which is placed into the treatment unit for the blood treatment.

Moreover, the blood treatment device comprises means for collecting blood and means for storing gas, in particular air. The means for collecting blood and for storing gas are in each case a reservoir which forms a closed-off volume, for example a blood and air chamber with a predetermined volume.

The means for collecting blood is connected to the means for storing gas so that, in the arterial phase during the filling of the means for collecting blood, air expelled from the means for collecting blood can pass into the means for storing gas and, in the venous phase, air from the means for storing gas can pass into the means for collecting blood, as a result of which the blood previously collected in the arterial phase is expelled from the means for collecting blood. The effect of this is that blood is removed from the patient in the arterial phase and the patient's blood treated in the blood treatment unit is returned back to the patient in the venous phase.

The connection between the means for collecting blood and the means for storing gas comprises a first and second connection path. The first connection path connects the means for collecting blood to the means for storing gas in such a way that, in the arterial phase, air expelled from the means for collecting blood is transferred to the means for storing gas, means for interrupting the connection being provided in the first connection path. The second connection path connects the means for collecting blood and storing gas in such a way that, in the venous phase, air stored in the means for storing gas is transferred to the means for collecting blood. The second connection path contains means for compressing gas, so that the air stored in the means for storing gas can be transferred into the means for collecting blood. With the means for compressing the air, a predetermined pressure can be built up in the means for collecting blood both during the arterial and the venous phase. The means for compressing gas can be designed for example as a conventional compressor.

The means for collecting blood and storing gas form together with the first and second connection path a closed-off volume, into which no gas can enter and from which no gas can exit. The closed-off volume is ventilated/deaerated solely for the purpose of initializing the system. The first connection path and the second connection path can be formed by separate lines. The first and second connection paths can however also comprise a common line segment.

An air infusion into the patient can be eliminated with greater reliability by the fact that there is established in the means for storing gas a pressure which in no case of operation is greater than the pressure that is established in the means for collecting blood. The effect of this is that air can pass from the means for storing gas into the means for collecting blood solely with the means for compressing gas. In the event of failure of the means for compressing gas, for example a leakage of the compressor, no air can on the other hand pass into the means for collecting blood. The situation is thus eliminated where the means for collecting blood run empty unintentionally, as a result of which air could pass into the patient.

In practice, an attempt is made to ensure that the return pressure with which blood is expelled from the means for collecting blood can be adjusted as low as possible, whereas the stroke volume is as large as possible. In order to be able to satisfy the condition that, in the event of failure of the compressor, air cannot pass from the means for storing gas into the means for collecting blood with a low return pressure and a large stroke volume, the system for initializing the successive arterial and venous phases is relieved to a predetermined pressure, preferably the ambient pressure, at the time of the change-over from the arterial to the venous phase, i.e., at the time of the upper change-over point at which the means for collecting blood are filled. In the successive arterial and venous phases, therefore, the pressure in the means for storing gas always lies below the predetermined pressure, in particular the ambient pressure, to which the closed off-system has been relieved.

During the arterial phase, the means for storing gas are not in direct contact with the patient, since the extracorporeal blood circuit is separated on the venous side, for example with a hose clamp. The course of the pressure in the means for storing gas thus plays a rather lesser role for patient safety during the arterial phase. It is decisive, however, that at the end of the arterial phase, i.e., at the start of the venous phase, the desired return pressure is present in the means for collecting blood. This is preferably achieved by the fact that the arterial phase is divided into two time intervals. In a preset first time interval, a connection is made between the means for collecting blood and the means for storing gas, so that the air expelled during the filling of the means for collecting blood passes into the means for storing gas, as a result of which a specific pressure is built up there. In a preset second interval, however, the connection between the means for collecting blood and storing gas is interrupted. The pressure in the means for storing gas thus remain constant, whereas the pressure in the means for collecting blood rises further, since blood is continuously conveyed into the means for collecting blood in the arterial phase. Two separate air volumes thus result.

In a preferred embodiment of the blood treatment device according to the present invention, the second connection path between the means for storing gas and collecting blood comprises a line for conveying gas, which connects the means for storing gas to the means for collecting blood. The means for compressing gas, for example a compressor, are disposed in this line. The first connection path comprises a bypass line bypassing the means for compressing gas, in which bypass line a bypass valve is disposed. When the means for compressing gas are not operated, the closed-off volume of the means for collecting blood are separated from the closed-off volume of the means for storing gas when the bypass valve is closed. When the bypass valve is opened, on the other hand, the two volumes form a common closed-off volume.

In a further preferred embodiment, the line for conveying gas comprises a first line segment, which connects the means for collecting blood to the pressure side of the means for compressing gas, and a second line segment, which connects the suction side of the means for compressing gas to the means for storing gas.

For the relief of the closed-off volume to the ambient pressure during the initialisation of the system, means for ventilation or deaeration are preferably provided in the first line segment.

The means for collecting blood are preferably designed as a container with a predetermined volume, which has an inlet and an outlet and is disposed in the blood return line of the extracorporeal circuit. The means for storing gas are preferably designed as a container with a predetermined volume.

The blood in the extracorporeal circuit is preferably conveyed by means of a blood pump which is disposed in the blood supply line.

A particular advantage of the blood treatment apparatus according to the present invention lies in the fact that the level of the means for collecting blood can be ascertained as accurately as possible without level sensors solely on the basis of pressure measurements. A preferred embodiment of the blood treatment device according to the present invention comprises means for measuring the pressure in the closed-off volume of the means for collecting blood, the closed-off volume in the connection paths between the means for collecting blood on the one hand and the means for compressing gas on the other hand and the closed-off volume of the means for storing gas, the blood volume being calculated from the measured pressure values.

In order to determine the pressure in the connection paths between the means for collecting blood on the one hand and the means for compressing gas on the other hand, the pressure can be measured either in a line segment of the first connection path and/or in a line segment of the second connection path, wherein the line segments extend between the means for collecting blood on the one hand and the means for compressing gas or the means for interrupting the connection on the other hand. If the first and second connection paths have a common line segment, it is also possible to measure the pressure in the common line segment of the two connection paths with a pressure sensor.

An example of embodiment of the present invention is explained in greater detail below by reference to the drawings.

DETAILED DESCRIPTION

Figure 1:
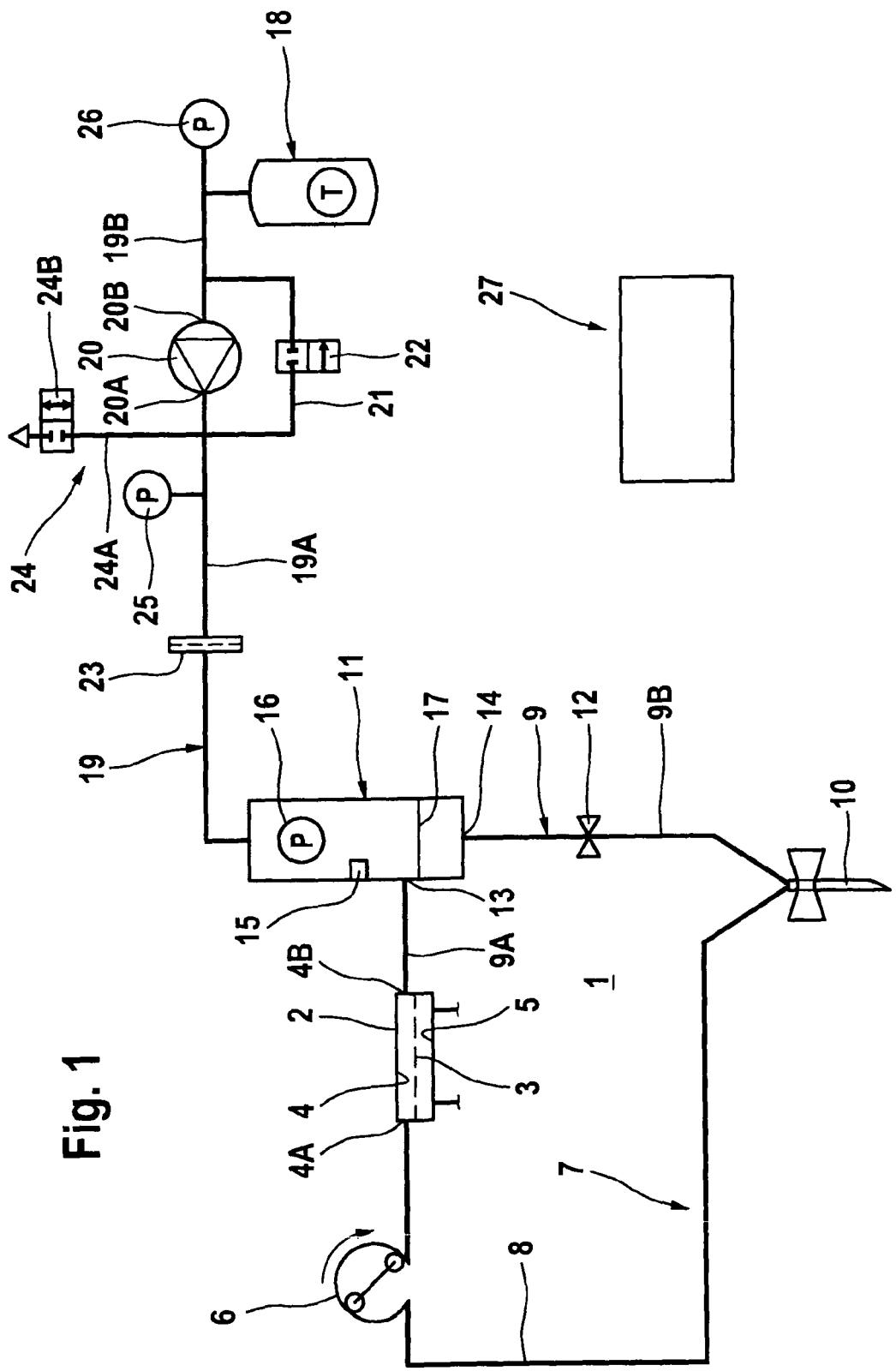
FIG. 1 shows an example of embodiment of the blood treatment device according to an example embodiment of the present invention for the single-needle operation in a very simplified schematic representation.

FIG. 1 shows the main components of a blood treatment device, in particular a dialysis apparatus, for the single-needle operation in a schematic representation.

During the blood treatment, the dialysis apparatus comprises an extracorporeal blood circuit 1, which includes a blood treatment unit 2, for example a dialyser, designed as a disposable. Dialyser 2 is divided by a semipermeable membrane 3 into a blood chamber 4 and a dialysing fluid chamber 5.

In the extracorporeal blood circuit, the blood is conveyed by means of a blood pump 6, which is part of the dialysis apparatus. The dialysing fluid circuit is not represented in FIG. 1.

Inserted into the dialysis apparatus is a hose set 7, which is disposed of after the treatment. Disposable 7 has a blood supply line 8 leading to inlet 4A of blood chamber 4 of dialyser 2, said blood supply line being inserted into roller pump 6 of the dialysis apparatus, and a blood return line 9 departing from outlet 4B of the blood chamber. Blood supply line and blood return line 8, 9 are connected to a common cannula 10 (needle).

Disposed in blood return line 9 of the disposable are means 11 for collecting blood, which are designed as a container with a predetermined volume.

The means for collecting blood are referred to in the following as a blood collecting container or blood storage unit.

Means 12 for interrupting the blood return line, for example a venous hose clamp, are disposed downstream of blood collecting container 11 on blood return line 9.

Blood collecting container 11 has an inlet 13, to which a first segment 9A of blood return line 9 leads, and has an outlet 14, from which a second segment 9B of blood return line 9 departs. For the detection of a specific level in blood collecting container 11, the dialysis apparatus has a level indicator 15, which detects when the level in the container reaches a preset value. A pressure transmitter 16 is also provided, which measures the pressure in blood collecting container 11.

When blood collecting container 11 is filled with blood, a specific air volume remains above liquid level 17 in the blood storage unit. The blood storage unit is in a flow connection with means 18 for storing gas, in particular air, which are designed as a container with a closed-off volume. Means 18 for storing gas are referred to in the following as an air storage container or air storage unit.

In order that the blood storage unit and air storage unit can communicate with one another, a line 19 which leads to air storage unit 18 departs from the upper side of blood storage unit 11. Disposed in line 19 is means 20 for compressing gas, which can be designed for example as a conventional compressor. As long as the compressor is not being operated, the compressor interrupts the flow connection between the blood storage unit and the air storage unit. When the compressor is operating, on the other hand, air present in the air storage unit is transferred into the blood storage unit. Since the air is compressed, a predetermined pressure is built up in the blood storage unit.

Line 19 has two line segments 19A, 19B, whereof one line segment 19A connects blood storage unit 11 to pressure-side connection 20A of compressor 20 and other line segment 19B connects suction-side connection 20B of compressor 20 to air storage unit 18. These line segments 19A, 19B form a connection path for the transfer of gas out of the air storage unit into the blood storage unit.

In order to be able to transfer air from the blood storage unit into the air storage unit when the compressor is not in operation, a bypass line 21 is provided which departs from first line segment 19A of line 19 and leads to second line segment 19B of line 19. A bypass valve 22 is incorporated into bypass line 21. Together with the corresponding line segments of line 19, bypass line 21 forms a connection path for conveying gas out of the blood storage unit into the air storage unit.

In order to prevent liquid from passing from the blood storage unit into the air storage unit, there is disposed in first line segment 19A of line 19 a filter 23, which contains a hydrophobic membrane, i.e. permeable to air, but impermeable to liquid. Since the blood storage unit is filled only up to a maximum level, however, liquid can in any case only pass into line 19 in the event of a malfunction.

For the ventilation/deaeration of the closed-off volume, which includes the blood storage unit and the air storage unit as well as line 19, means 24 is provided for ventilation/deaeration, which comprise a ventilation/deaeration line 24 with a ventilation/deaeration valve 24B, said ventilation/deaeration line being connected for example to first line segment 19A of line 19. Ventilation/deaeration line 24A can in principle depart from any point of the volume to be ventilated or deaerated. The ventilation/deaeration should in particular take place in the part on the machine side.

Apart from pressure transmitter 16 for measuring the pressure in the blood storage unit, a pressure transmitter 25 is provided for measuring the pressure in first line segment 19A of line 19 between filter 23 and compressor 20 and a further pressure transmitter 26 is provided for measuring the pressure in air storage unit 18. A temperature sensor T for measuring the temperature of the air in the air storage unit is provided in the air storage unit.

The dialysis apparatus has a central control and computing unit 27, which is connected via electrical lines (not shown) to blood pump 6, venous hose clamp 12, bypass valve 22, ventilation/deaeration valve 24B, level indicator 15, compressor 20 and pressure transmitters 16, and 26. The central control and computing unit is in turn connected to an input unit (not shown), which creates an interface between the user and the machine.

The operation of the dialysis apparatus is described below in detail by reference to FIGS. 2 and 3. Central control and computing unit 27 controls the dialysis machine as follows.

At the start of the actual dialysis treatment, an initialization of the system takes place with the following process steps.

Figure 2:
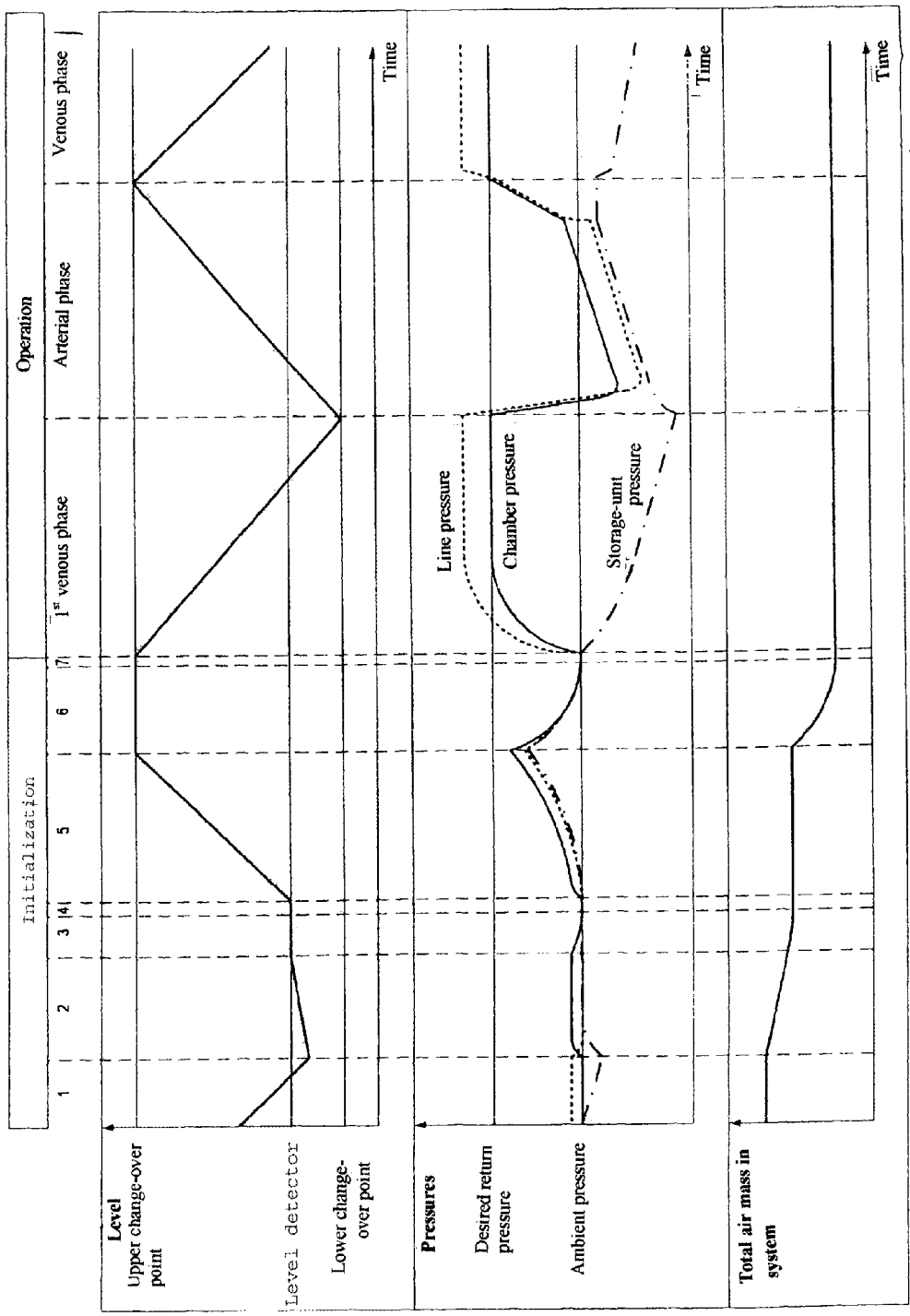
FIG. 2 shows the course of the level and the pressure during the initialization and the operation of the blood treatment device according to the example embodiment of the present invention.

FIG. 2 shows the level in the blood storage unit as a function of time during the individual phases of the initialization. Moreover, FIG. 2 shows the course of the pressure in the blood storage unit, which is referred to as the chamber pressure, the pressure in the air storage unit, which is referred to as the storage-unit pressure, and the pressure in first line segment 19A of line 19, which is referred to as the line pressure. Furthermore, FIG. 2 shows the time-related course of the total air mass enclosed in the blood storage unit and in the air storage unit as well as the corresponding segments of lines 19, 22.

In the first initialization step, the blood level in the blood storage unit is lowered below a specific level, which lies between the change-over point, at which the change-over is to take place from the arterial phase to the venous phase during the operation of the dialysis apparatus, and the lower change-over point, at which the change-over from the venous to the arterial phase is to take place. For this purpose, control and computing unit 27 opens venous hose clamp 12 with blood pump 6 standing still and puts compressor 20 into operation until the desired liquid level is reached, which is detected by the level indicator. FIG. 2 shows that the level falls, whilst the total air mass in the system remains constant. This step can be skipped if the blood level is already located below the desired level.

In the second step, the blood level is then adjusted to the desired level, which is detected by the level indicator. For this purpose, bypass valve 22 and ventilation/deaeration valve 24B is opened and blood pump 6 is operated with venous hose clamp closed until the desired level is reached. FIG. 2 shows that the level rises to the desired level, whilst the air mass in the system diminishes.

When the desired level is reached, there is a waiting time until the chamber pressure and storage-unit pressure, as well as the line pressure, have become adjusted to ambient pressure. The level thereby remains constant, whilst the air mass continues to diminish slightly (step 3). Only then is ventilation/deaeration valve 24B closed again (step 4).

The blood storage unit then continues to be filled with blood. With the bypass valve opened, blood pump 6 is operated until such time as the level in the blood storage unit has reached the level of the upper change-over point (step 5). The air mass in the system thereby remains constant. Since the chamber and storage-unit pressure and the line pressure are measured by means of the pressure transmitters, the level in the blood storage unit may be continuously calculated. The control and computing unit calculates the level in the blood storage unit and stops the blood pump when the level has reached the level of the upper change-over point. This will be described in detail below.

After the control and computing unit has stopped blood pump 6, ventilation/deaeration valve 24B is opened again, so that the pressure built up in the system is relieved to the ambient pressure (step 6). FIG. 2 shows that the level remains constant, whilst the chamber and storage-unit pressure as well as the line pressure fall to ambient pressure. Since the volume that is enclosed by the system, i.e. both the volume of the blood storage unit and the air storage unit as well as the lines, and also the pressures in the system are known, the air mass contained in the system can be calculated. This will be described in detail below.

Ventilation/deaeration valve 24B is closed as the last step of the initialisation, whereby neither the level nor the pressures and the air mass in the system change (step 7). The ventilation/deaeration valve remains closed throughout the whole blood treatment unless a renewed initialization is required, for example after the detection of an air leak. The initialization is thus completed, and the blood treatment starts with the first venous phase.

In the first venous phase, compressor 20 is operated with bypass valve 22 closed, venous hose clamp 12 being opened and blood pump 6 standing still. During the operation of the compressor, air from storage unit 18 is compressed and fed to blood storage unit 11. The chamber pressure and line pressure thus increase, whereas the storage-unit pressure diminishes. At the same time, the level in the blood storage unit diminishes continuously, until the level of the lower change-over point is reached. It is decisive here that the storage-unit pressure lies below the chamber pressure and therefore also below the line pressure, in order to prevent an entry of gas from the air storage unit into the blood storage unit in the event of a malfunction. In addition, an attempt is made to ensure that the storage-unit pressure lies even below the ambient pressure.

The arterial phase then begins, in which the blood storage unit is again filled with blood taken from the patient, this again being followed by the venous phase in which the blood is fed from the blood storage unit back to the patient.

The air storage unit is dimensioned with a size such that sufficient air is also present in the system at the end of the venous phase, in order to be able to maintain the desired return pressure in the blood storage unit. In order to be able, with the same initialisation, to adjust all the operating points with a return pressure of 0 to 500 mmHg relative with a stroke volume up to 60 ml, an air storage unit with a storage volume of approx. 300 ml is required in practice.

Figure 3:
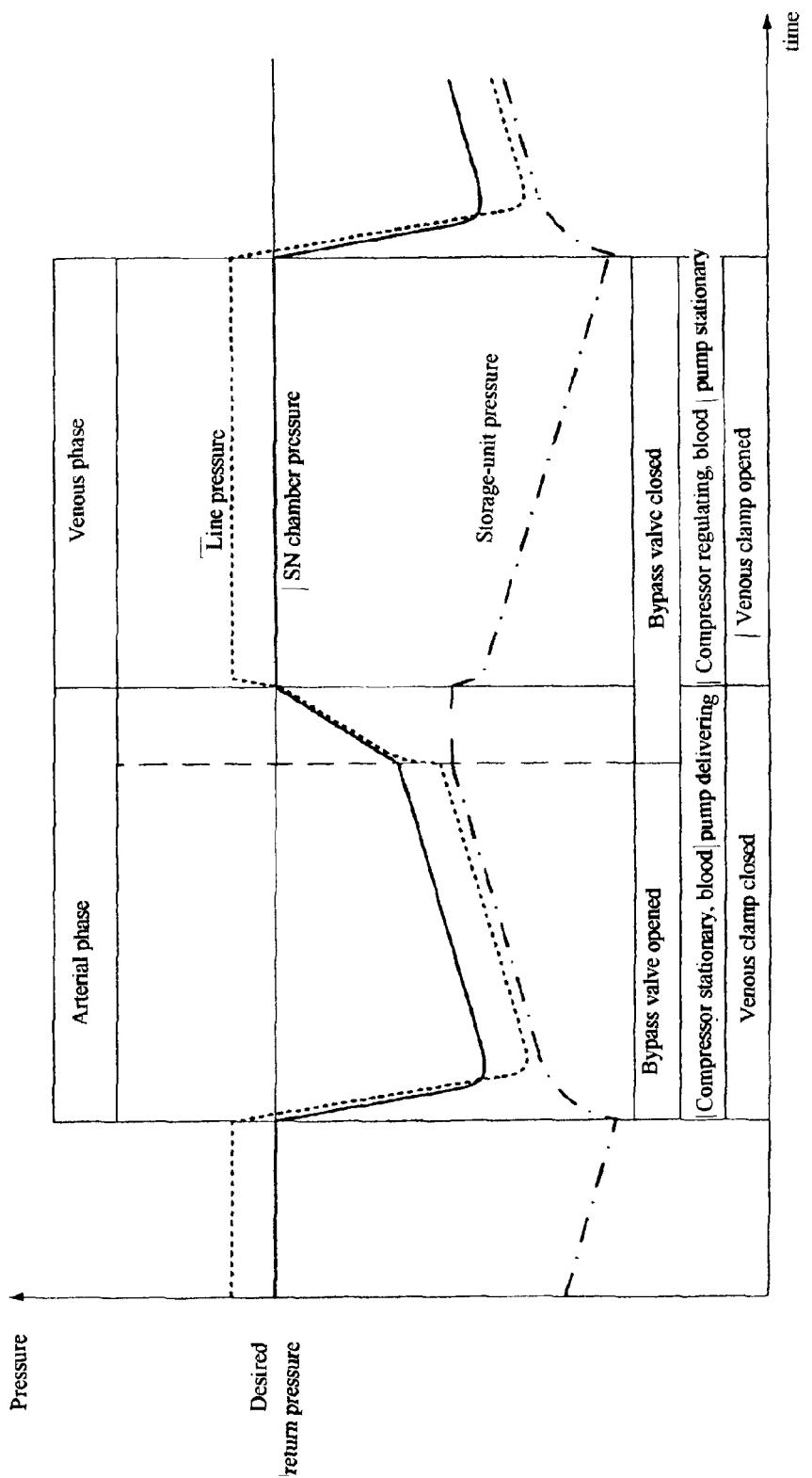
FIG. 3 shows the course of the pressure during the successive arterial and venous phases after the initialization.

The time-related course of the chamber pressure and storage-unit pressure as well as the line pressure during the actual arterial and venous phases after the initialisation of the system is represented in FIG. 3, which shows a detail from FIG. 2.

Blood pump 6 is operated throughout the whole arterial phase, compressor 20 standing still. Venous hose clamp 12 remains closed throughout the whole arterial phase.

At the start of the arterial phase, control and computing unit 27 opens bypass valve 22, so that the air expelled out of blood storage unit 11 passes via bypass line 21 into air storage unit 18. The storage-unit pressure therefore increases, whilst the chamber and line pressure at first falls, after which it also then rises, as it were, with the storage-unit pressure. The air mass contained in the blood storage unit and in the respective line volume therefore constantly diminishes.

As soon as the air mass contained in the blood storage unit and the line volume has reached a predetermined amount, which results from the desired stroke volume and the desired return pressure, the control and computing unit closes the bypass valve. Two separate air volumes thus arise, i.e. the air volume of the blood storage unit with the respective line segments and the volume of the air storage unit with respective line segments. The blood pump is then operated with the bypass valve closed, so that the storage-unit pressure remains constant, whilst the air in the blood storage unit and the respective line volume is compressed until, upon reaching the desired stroke volume, the desired return pressure is also reached. FIG. 3 shows that the chamber and line pressure have risen to the desired return pressure at the end of the arterial phase, whereby the storage-unit pressure throughout the whole arterial phase always lies below the chamber and line pressure, in particular below the ambient pressure. This thus rules out air passing from the air storage unit into the blood storage unit even in the event of a malfunction of the system, for example with a leakage of the compressor.

Instead of the division of the arterial phase into a first and second time interval, other embodiments are also possible with which the advantages according to the present invention can also be achieved. An alternative embodiment makes provision to use, instead of bypass valve 22, a pressure-controlled valve which opens when a threshold pressure corresponding to the return pressure is reached, so that a constant pressure prevails in the blood storage unit in a certain time period.

The control and computing unit then changes over to the venous phase, whereby the bypass valve remains closed, the blood pump is stopped and the compressor put into operation and the venous hose clamp is opened. The compressor is operated throughout the whole venous phase, the blood pump standing still. The venous hose clamp remains open and the bypass valve closed during the venous phase.

The compressor conveys air out of the air storage unit into the blood storage unit in order to build up an excess pressure, so that blood is conveyed from the blood storage unit. The compressor is operated in such a way that the desired return pressure is established in the blood storage unit. Since air from the air storage unit is continuously fed to the blood storage unit, the storage-unit pressure continuously diminishes. The decisive factor again is that the storage-unit pressure always lies below the chamber and line pressure, preferably also below the ambient pressure, so that an air infusion out of the air storage unit into the patient is ruled out in the event of a malfunction. The venous phase is ended when the blood level in the blood storage unit has again fallen to the level of the lower change-over point. The next arterial phase then follows.

The calculation of blood volume $V_{blood}$ present in the blood storage unit is described below, said calculation being carried out continuously or in preset intervals by the control and computing unit during the operation of the dialysis apparatus. If the blood volume is known, this can be used for comparison with the change-over points from the arterial to the venous phase or vice versa.

In order to calculate blood volume $V_{blood}$ present in the blood storage unit, it is first necessary to determine the air mass in the blood storage unit. After pressure equalisation has taken place, the following holds:

$$pV = \frac{m}{M_n} RT$$

with:
p=pressure (absolute), V=volume, m=mass, $M_m$=molar mass,
R=general gas constant and T=temperature Since $M_m$ and R are constant and no absolute values are required for the air mass, the latter do not need to be taken into account explicitly. Accordingly, only the following has to be determined:

$$\frac{pV}{T} \equiv m.$$

In order to determine the total air mass, the sum of all the partial air masses, i.e. the air mass in the blood storage unit, the respective lines and the air storage unit, must be calculated. For this purpose, all volumes filled with air must be multiplied by the given prevailing pressure and divided by the temperature.

$$\left(\frac{pV}{T}\right)_{total} = \frac{P_{blood\ storage\ unit} \cdot V_{blood\ storage\ unit/air}}{T_{blood\ storage\ unit}} +$$

$$\frac{P_{line} \cdot V_{line}}{T_{line}} + \frac{P_{air\ storage\ unit} \cdot V_{air\ storage\ unit}}{T_{air\ storage\ unit}}$$

$$T_{blood\ storage\ unit} \approx 273.15\ K + 36\ K$$

$$T_{line} \approx \frac{T_{blood\ storage\ unit} + T_{air\ storage\ unit}}{2}$$

The air volume of the blood storage unit $V_{blood\ storage\ unit/air}$ changes during operation. If the blood level is at height H of the level detected by level indicator 15, the following holds:

$$V_{blood\ storage\ unit/air} = V_{blood\ storage\ unit/air\ UT} - \Delta V_{blood\ storage\ unit/UT-H}.$$

where $V_{blood\ storage\ unit/air\ UT}$ is the air volume in the blood storage unit at lower change-over point UT and $\Delta V_{blood\ storage\ unit/UT-H}$ is the volume difference between lower change-over point UT and the height of the level in the blood storage unit detected by level indicator 15.

At the end of the initialisation at upper change-over point OT, blood with the total stroke volume $V_{stroke}$ is additionally present in the blood storage unit, so that $$V_{blood\ storage\ unit/air} = V_{blood\ storage\ unit/air\ UT} - V_{stroke}.$$

The remaining volumes remain constant. To a good approximation, the temperatures can be put as constant if no temperature compensation takes place. Preferably, however, a temperature sensor is provided for the temperature measurement at least in the air storage unit, so that a temperature compensation can be carried out. Temperature sensors can however also be provided for other pressure values.

Delivered blood volume $V_{blood}$ in the blood storage unit is calculated with each program loop during the whole cycle. Air volume $V_{blood\ storage\ unit/air}$ enclosed in the blood storage unit is calculated with the aid of the measured pressures and the difference is taken between the air volume in the blood storage unit at lower change-over point UT and the air volume of the blood storage unit.

$$V_{blood\ storage\ unit/air} = \frac{\left(\frac{pV}{T}\right)_{ges} - \frac{P_{line}V_{line}}{T_{line}} - \frac{P_{air\ storage\ unit}V_{air\ storage\ unit}}{T_{air\ storage\ unit}}}{\frac{P_{blood\ storage\ unit}}{T_{blood\ storage\ unit}}}$$

$$V_{blood} = V_{blood\ storage\ unit/air\ UT} - V_{blood\ storage\ unit/air}.$$

The total air mass $(pV/T)_{total}$ remains unchanged after the initialization of the system, because the ventilation valve remains closed. Since the calculation of blood volume $V_{blood}$ takes place with the blood pump running or compressor running, a smoothing-out of the pressure signals and calculated blood volume $V_{blood}$ is performed.

The change-over from the arterial to the venous phase (OT) takes place when the difference between calculated blood volume $V_{blood}$ and adjusted stroke volume $V_{stroke}$ is equal to zero, and the change-over from the venous to the arterial phase takes place when the calculated blood volume is equal to zero.

It is described below how the control and computing unit calculates the time at which, within the arterial phase, the change-over takes place between the first and second time interval of the arterial phase.

As already described above, the change-over point from the arterial to the venous phase and back is possible by a simple comparison of the blood volume with the stroke volume, i.e. zero. The arterial phase is divided, as already mentioned, into a first and a second time interval. In the first arterial phase, the blood pump conveys blood via the dialyser with the bypass valve open into the blood storage unit. The underpressure, which has previously built up in the air storage unit in the venous phase, is used to assist the pump. In the second arterial phase, the air storage unit is decoupled from the remaining system by closing the bypass valve, and the pressure in the blood storage unit increases sharply due to the delivered blood volume. At the end of the second arterial phase, the desired setpoint pressure should be present in the blood storage unit. The change-over point between the first and second arterial phase, therefore, must be selected in such a way that the still outstanding blood volume up to upper change-over point OT builds up the setpoint pressure in the blood storage unit and in the line.

Accordingly, it is necessary to calculate the air mass that builds up setpoint pressure $p_{setpoint}$ with compression on the air volume available in the blood storage unit and the line at upper change-over point OT. The air mass in the blood storage unit and line is $$\frac{P_{blood\ storage\ unit} V_{blood\ storage\ unit}}{T_{blood\ storage\ unit}} + \frac{P_{line} V_{line}}{T_{line}} = \left(\frac{pV}{T}\right)_{total} - \frac{P_{air\ storage\ unit} V_{air\ storage\ unit}}{T_{air\ storage\ unit}}$$

At the change-over point from the first to the second time interval of the arterial phase, the air mass present in the blood storage unit and line must be equal to the air mass which is present in the blood storage unit and the line at upper change-over point OT.

$$\left(\frac{pV}{T}\right)_{total} = \frac{P_{air\ storage\ unit} V_{air\ storage\ unit}}{T_{air\ storage\ unit}} = \frac{P_{setpoint} \cdot V_{blood\ storage\ unit/airOT}}{T_{blood\ storage\ unit}} + \frac{P_{setpoinit} \cdot V_{line}}{T_{line}}$$

Here, $V_{blood\ storage\ unit/airOT}$ is the air volume in the blood storage unit at upper change-over point OT.

The control and computing unit checks during the arterial phase whether the above equation is satisfied. As soon as the equation is satisfied, the second time interval of the arterial phase begins, the bypass valve being closed. The blood pump is operated by the control and computing unit in the second time interval at the same delivery rate, until the desired stroke volume and thus the upper change-over point OT is reached.

A leakage in the closed-off volume can lead to a change in the gas quantity enclosed in the system. If the leakage lies in the excess-pressure region of the system, i.e. in the region of the blood storage unit or the adjacent line segments, the leakage leads to a reduction in the enclosed air quantity, as a result of which the level of the blood in the blood storage unit increases. There is the risk of the blood storage unit filling up and the blood level rising up to the hydrophobic membrane, so that the arterial phase can no longer be terminated properly. Conversely, if there is a leakage in the underpressure region, i.e. in the gas storage unit or through air entry from the blood system, the enclosed air quantity is increased, so that the level of the blood in the blood storage unit falls. This can lead to the blood level falling too rapidly in the venous phase, which can lead to undesired foaming, in the extreme case even to the air alarm. This can however be monitored by the fact that the air quantity enclosed in the system is observed. Such monitoring of the air quantity can be provided for with the device according to the present invention.

The monitoring of the air quantity for the detection of a leakage takes place by the fact that the time is detected at which the level indicator 15 in blood storage unit 11 detects the level, i.e. at which the blood reaches the preset level. The actual level of the blood is thus known for this time. This value is compared with the level calculated at this time from the pressure values. If the difference between the measured and calculated level is greater than a preset threshold value, the air quantity enclosed in the system has changed significantly, which can be traced back to a leakage in the system. In this case, the system is reinitialized. If the case of the fault occurs too frequently, central control and computing unit 27 interrupts the treatment.

An alternative evaluation makes provision such that it is not the measured and calculated level that is taken into account, but rather the time at which the level indicator 15 detects the preset level is compared with the calculated time at which the preset level should be established. If a significant time difference is present, it is concluded that there is a leakage in the system.

Another embodiment also makes provision to detect a leakage in the system in the part facing away from blood storage unit 11 behind filter 23 after the increase in the level above the level detected by the level indicator in the arterial phase, by the fact that an excessively sharply increasing pressure is detected by pressure sensor 16 in blood storage unit 11, whereby the pressure and/or the pressure rise per unit of time exceeds a preset threshold value. In this case, the blood reaching the filter leads to a pressure increase, which drastically reduces the compliance in this part of the system. This applies in particular to the case in which a pressure sensor is used which measures the pressure in direct contact, i.e. without a compressible intermediate space.

The invention claimed is:

1. A device for blood treatment in a single-needle operation, comprising:
    a pump configured to convey blood in an extracorporeal blood circuit to a blood container configured to collect blood, whereby the extracorporeal blood circuit has a blood supply line leading to an inlet of a blood treatment unit and a blood return line departing from an outlet of the blood treatment unit, and the blood container has a closed-off volume;
    a gas container having a closed-off volume;
    a first connection path for connecting the blood container to the gas container in such a way that, in an arterial phase, gas expelled from the blood container during the filling of the blood container is transferred to the gas container, the first connection path containing a valve configured to interrupt the connection;
    a second connection path, containing a gas compressor, for connecting the gas container to the blood container in such a way that, for the purpose of emptying the blood container, gas stored in the gas container is transferred by the gas compressor to the blood container, so that blood can be fed to the extracorporeal blood circuit in the arterial phase and removed from the extracorporeal blood circuit in the venous phase; and
    a computing arrangement configured to determine blood volume $V_{blood}$ enclosed in the blood container, wherein the computing arrangement includes:
        a first pressure transmitter configured to measure the pressure in the blood container;
        a second pressure transmitter configured to measure the pressure in the first and second connection paths between the blood container and the gas compressor; and
        a third pressure transmitter for measuring the pressure in the gas container,
        wherein the computing arrangement is configured to calculate the blood volume $V_{blood}$ on the basis of a) the measured pressure in the closed-off volume of the blood container, b) the closed-off volume of the first and second connection paths between blood container and the gas compressor, and c) the closed-off volume of the as container.

2. The blood treatment device according to claim 1, wherein:
the first connection path includes a bypass line bypassing the gas compressor, a bypass valve being disposed in the bypass line; and
the second connection path includes a gas line for conveying gas, the gas line connecting the blood container to the gas container, the gas compressor being disposed in the gas line.

3. The blood treatment device according to claim 2, wherein the gas line includes a first line segment that connects the blood container to a pressure-side of the gas container, and a second line segment that connects a suction-side of the gas compressor to the gas container, a ventilation valve being provided for the ventilation/deaeration of the first line segment.

4. The blood treatment device according to claim 1, wherein the blood container has a predetermined volume and is disposed in the blood return line of the extracorporeal circuit.

5. The blood treatment device according to claim 1, wherein the gas container has a predetermined volume.

6. The blood treatment device according to claim 1, wherein the pump is a blood pump disposed in the blood supply line.

7. The blood treatment device according to claim 1, further comprising a control unit configured to change over between the arterial phase and the venous phase, the control unit configured such that
the pump is operated in the arterial phase, whereby the blood container is connected via the first connection path to the gas container, so that gas expelled from the blood container during the filling of the blood container is transferred to the gas container, and
the gas compressor is operated in the venous phase, wherein the gas container is connected via the second connection path to the blood container, so that, for the purpose of emptying the blood container, gas stored in the gas container is transferred by the gas compressor to the blood container.

8. The blood treatment device according to claim 7, wherein the control unit is configured such that, in the arterial phase, the valve for interrupting the first connection path is actuated in a first time interval in such a way that the first connection path is not interrupted, and the valve for interrupting the first connection path is actuated in a second time interval in such a way that the first connection path is interrupted.

9. A device for blood treatment in a single-needle operation, comprising:
a blood treatment unit including an inlet and an outlet;
an extracorporeal blood circuit including a blood supply line leading to the inlet of a blood treatment unit and a blood return line departing from the outlet of the blood treatment unit;
a blood container configured to collect blood in the extracorporeal circuit, the blood container having a closed-off volume;
a pump configured to convey blood in the extracorporeal circuit to the blood container;
a gas container configured to store gas, the gas container having a closed-off volume; and
a computing arrangement configured to determine blood volume $V_{blood}$ enclosed in the blood container, wherein the computing arrangement includes:
a first pressure transmitter configured to measure the pressure in the blood container;
a second pressure transmitter configured to measure the pressure in the first and second connection paths between the blood container and the gas compressor; and
a third pressure transmitter for measuring the pressure in the gas container,
wherein the computing arrangement is configured to calculate the blood volume $V_{blood}$ on the basis of a) the measured pressure in the closed-off volume of the blood container, b) the closed-off volume of the first and second connection paths between blood container and the gas compressor, and c) the closed-off volume of the gas container,
wherein
the blood container is connected, via a first connection path having a valve for interrupting the connection, to the gas container in such a way that, in an arterial phase, gas expelled from the blood container during the filling of the blood container is transferred to the gas container, and
the blood container is connected, via a second connection path having a gas compressor, to the gas container in such a way that, for the purpose of emptying the blood container in a venous phase, gas stored in the gas container is transferred by the gas compressor to the blood container,
so that blood can be fed to the extracorporeal blood circuit in the arterial phase and blood can be removed from the extracorporeal blood circuit in the venous phase.

10. The device according to claim 9, wherein:
the first connection path includes a bypass line bypassing the gas compressor, a bypass valve being disposed in the bypass line; and
the second connection path includes a gas line for conveying gas, the gas line connecting the blood container to the gas container, the gas compressor being disposed in the gas line.

11. The device according to claim 10, wherein the gas line includes a first line segment that connects the blood container to a pressure-side of the gas container, and a second line segment that connects a suction-side of the gas compressor to the gas container, a ventilation valve being provided for the ventilation/deaeration of the first line segment.

12. The device according to claim 9, wherein the blood container has a predetermined volume and is disposed in the blood return line of the extracorporeal circuit.

13. The device according to claim 9, wherein the gas container has a predetermined volume.

14. The device according to claim 9, wherein the pump is a blood pump disposed in the blood supply line.

15. The device according to claim 9, further comprising a control unit configured to change over between the arterial phase and the venous phase, the control unit configured such that
the pump is operated in the arterial phase, whereby the blood container is connected via the first connection path to the gas container, so that gas expelled from the blood container during the filling of the blood container is transferred to the gas container, and
the gas compressor is operated in the venous phase, whereby the gas container is connected via the second connection path to the blood container, so that, for the purpose of emptying the blood container, gas stored in the gas container is transferred by the gas compressor to the blood container.

16. The device according to claim 15, characterised in that the control unit is configured such that, in the arterial phase, the valve for interrupting the first connection path is actuated in a first time interval in such a way that the first connection path is not interrupted, and the valve for interrupting the first connection path is actuated in a second time interval in such a way that the first connection path is interrupted.

* * * * *